US010252087B2

(12) United States Patent
Song

(10) Patent No.: US 10,252,087 B2
(45) Date of Patent: Apr. 9, 2019

(54) HAIR DARKENING DYE COMPOSITION

(71) Applicant: Jilin Hengtai Garment Washing and Dyeing Science and Technology Institute, Changchun, Jilin (CN)

(72) Inventor: Zikui Song, Jilin (CN)

(73) Assignee: Jilin Hengtai Garment Washing and Dyeing Science and Technology Institute, Changchun (CN)

( * ) Notice: Subject to any disclaimer, the term of this patent is extended or adjusted under 35 U.S.C. 154(b) by 0 days.

(21) Appl. No.: 15/536,654

(22) PCT Filed: Feb. 24, 2016

(86) PCT No.: PCT/CN2016/074428

§ 371 (c)(1),
(2) Date: Jun. 16, 2017

(87) PCT Pub. No.: WO2016/161852

PCT Pub. Date: Oct. 13, 2016

(65) Prior Publication Data

US 2017/0348548 A1 Dec. 7, 2017

(30) Foreign Application Priority Data

Apr. 9, 2015 (CN) .......................... 2015 1 0166807

(51) Int. Cl.

*A61Q 5/10* (2006.01)
*A61K 8/73* (2006.01)
*A61K 8/89* (2006.01)
*A61K 8/06* (2006.01)

(52) U.S. Cl.

CPC .................. *A61Q 5/10* (2013.01); *A61K 8/06* (2013.01); *A61K 8/73* (2013.01); *A61K 8/89* (2013.01)

(58) Field of Classification Search

CPC ... A61Q 5/10; A61K 8/06; A61K 8/73; A61K 8/89

See application file for complete search history.

(56) References Cited

U.S. PATENT DOCUMENTS

2007/0251024 A1 11/2007 Greaves et al.

FOREIGN PATENT DOCUMENTS

| | | | | |
|---|---|---|---|---|
| CN | 101431976 A | 5/2009 | | |
| CN | 102268823 A | 12/2011 | | |
| CN | 102772336 A | 11/2012 | | |
| CN | 102972336 A | * 11/2012 | | A61K 8/73 |
| CN | 102973467 A | 3/2013 | | |

OTHER PUBLICATIONS

English translation (Aug. 9, 2018) of the Patent No. CN 102772336.*
International Search Report of PCT Patent Application No. PCT/CN2016/074428 dated May 27, 2016.
1st Office Action of counterpart Chinese Patent Application No. 201510166807.7 dated Dec. 30, 2016.
English translation of 1st Office Action of counterpart Chinese Patent Application No. 201510166807.7 dated Dec. 30, 2016.
Lingling Luo et al., Preparation and Applied Research on a New Hair Dye, Journal of Jiangnan University (Natural Science Edition), Aug. 15, 2007, pp. 483-486, vol. 6, No. 4.

* cited by examiner

*Primary Examiner* — Eisa B Elhilo

(57) ABSTRACT

A hair darkening dye composition, comprises: 2-98 parts by weight of hair dye; 1-99 parts by weight of darkening agent; 2-98 parts by weight of crosslinking agent; 2-98 parts by weight of emulsifier; 2-98 parts by weight of dyeing auxiliaries; and 0.1-40 parts by weight of pH regulator. The darkening agent is selected from one or more of chitin, chitosan, gelatin, silicon oil and resin. The chitin, chitosan and gelatin have a relative molecular weight of less than $2.7\times10^4$, and the silicon oil and resin have a refractive index of less than 1.55.

18 Claims, No Drawings

HAIR DARKENING DYE COMPOSITION

The present application claims the priority of the Chinese patent application filed with the Chinese Patent Office on Apr. 9, 2015, with the application number of 201510166807.7 and entitled "Hair Darkening Dye Composition", the entire contents of which are incorporated herein by reference.

TECHNICAL FIELD

The present invention relates to the technical field of hair dyeing, and particularly to a hair darkening dye composition.

BACKGROUND ART

Among the chemical hair dyes, the most widely used ones at present are oxidation-type hair dyes that contain more than twenty kinds of chemical components, e.g., p-phenylenediamine. In order to achieve the effect of sufficient dyeing depth, p-phenylenediamine is often used beyond the limitation during preparation; and when in use, the amount of the hair dyes is also increased by 2~3 times, and at the same time, the dyeing time is multiplied and the dyeing temperature is increased. As a result, excessive hair dyes come into contact with the skin and are then heated, which makes it easy for benzene organics to enter the body through the skin, and is unfavorable to the health of the body due to the long-term repeated effects.

Nowadays, people pursue health and advocate naturalness, and have an urgent desire for safe and non-toxic hair dyes that do not cause skin allergy. It has become one of the hair dye development directions to do research on and develop safe and non-toxic hair dyes. Then pure natural hair dyes came into being, the main ingredients of which are pure natural elements extracted from natural plants, minerals or animals, are harmless and non-toxic to the human body, do not generate primary irritation to hairs, and do not cause skin allergy.

The advantage of the pure natural hair dyes is that they do not damage the body, while the disadvantages thereof are that the dye uptake is relatively low, the color depth of the dyed hair is not sufficient, and a saturated color can hardly be achieved even after repetition of dyeing for several times, which prevents, to a great extent, the pure natural hair dyes from being widely used.

DISCLOSURE OF THE INVENTION

In view of the above, an object of the present invention is to provide a hair darkening dye composition. The hair darkening dye composition provided by the present invention has a darkening property, allowing an unsaturated color dyed by a pure natural hair dye to be darkened to a saturated color, and enabling a saturated color to be achieved by a relatively small amount of a chemical hair dye.

The present invention provides a hair darkening dye composition, comprising:

2~98 parts by weight of a hair dye;

1~99 parts by weight of a darkening agent, which is one or more selected from the group consisting of chitin, chitosan, gelatin, silicone oil and resin, wherein the chitin, chitosan and gelatin all have a relative molecular mass of $2.7\times10^4$ or less, and the silicone oil and resin both have a refractive index of 1.55 or less;

2~98 parts by weight of a crosslinking agent;

2~98 parts by weight of an emulsifier;

2~98 parts by weight of a dyeing auxiliary; and 0.1~40 parts by weight of a pH regulator.

Preferably, the crosslinking agent is one or more selected from the group consisting of cyanaldehyde, magnesium chloride, citric acid, glyoxal, the crosslinking agent EH, polyethylene glycol and the antistatic agent A-2ST.

Preferably, the hair darkening dye composition comprises 5~40 parts by weight of the crosslinking agent.

Preferably, the hair darkening dye composition comprises 4~45 parts by weight of the darkening agent.

Preferably, the darkening agent is selected from the group consisting of chitin, chitosan and gelatin.

The darkening agent is prepared by degradation using a degradation agent, wherein the degradation agent is selected from the group consisting of an acid degradation agent, an oxidative degradation agent and an enzyme degradation agent.

Preferably, the pH regulator is selected from the group consisting of an organic acid, an inorganic weak acid, an organic base and an inorganic weak base.

Preferably, the hair darkening dye composition comprises 2~60 parts by weight of a hair dye.

The hair dye is selected from the group consisting of pure natural hair dyes and chemical hair dyes.

Preferably, the emulsifier is selected from the group consisting of a zwitterionic emulsifier and a nonionic emulsifier.

Preferably, the dyeing auxiliary is selected from the group consisting of edible salt, sodium sulphate, alum, melanterite, chalcanthite, acetic acid, sodium carbonate and sodium bicarbonate.

Preferably, the hair darkening dye composition further comprises 2~98 parts by weight of an additive.

The additive is one or more selected from the group consisting of a leveling agent, an antistatic agent, an anticorrosion antibacterial agent and an essence.

Compared with the prior art, the hair darkening dye composition provided by the present invention is mainly composed of the following raw materials: 2~98 parts by weight of a hair dye; 1~99 parts by weight of a darkening agent; 2~98 parts by weight of a crosslinking agent; 2~98 parts by weight of an emulsifier; 2~98 parts by weight of a dyeing auxiliary; and 0.1~40 parts by weight of a pH regulator, wherein the darkening agent is selected from one or more of chitin, chitosan, gelatin, silicone oil and resin, the chitin, chitosan and gelatin all have a relative molecular mass of $2.7\times10^4$ or less, and the silicone oil and resin both have a refractive index of 1.55 or less. In the present invention, the hair dye may dye hair into a color with a certain depth; under the actions of the darkening agent, the crosslinking agent etc., the unsaturated color dyed by the pure natural hair dye can be deepened, and a saturated color with a sufficient depth is finally obtained, or the use amount of a chemical hair dye may be greatly reduced; moreover, the hair dyeing time may be shortened and the hair dyeing temperature may be reduced, thereby relatively reducing the harm to the human body, furthermore, the dyeing fastness may be improved, prolonging the dyeing interval and reducing the number of the times of repeated hair dyeing can be reduced. Thus, under the synergistic and comprehensive effects of all the raw materials, the hair darkening dye composition provided by the present invention has the properties of color darkening and fixation, such that an unsaturated color dyed by a pure natural hair dye is deepened into a saturated color and a saturated color may be achieved by a relatively small amount of a chemical hair dye.

DETAILED DESCRIPTION OF EMBODIMENTS

The present invention provides a hair darkening dye composition, comprising:

2~98 parts by weight of a hair dye;

1~99 parts by weight of a darkening agent, which is selected from one or more of chitin, chitosan, gelatin, silicone oil and resin, wherein the chitin, chitosan and gelatin all have a relative molecular mass of $2.7\times10^4$ or less, and the silicone oil and resin both have a refractive index of 1.55 or less;

2~98 parts by weight of a crosslinking agent;

2~98 parts by weight of an emulsifier;

2~98 parts by weight of a dyeing auxiliary; and 0.1~40 parts by weight of a pH regulator.

In the present invention, in the hair dye, a certain amount of a specific darkening agent is added, and the raw materials, such as the crosslinking agent and the pH regulator, are also added, so that when used for hair dyeing, the hair darkening dye composition provided by the present invention achieves the darkening effect with a small amount, which is beneficial to wide application.

The hair darkening dye composition provided by the present invention comprises 2~98 parts by weight of a hair dye, preferably comprises 2~60 parts by weight of a hair dye, which is in a small amount. The hair dye is preferably selected from pure natural hair dyes or chemical hair dyes, and more preferably, from pure natural hair dyes, wherein the pure natural hair dyes generally include plant hair dyes, mineral hair dyes and animal hair dyes. In the embodiments of the present invention, the plant hair dyes comprise carotenes, anthraquinones, naphthoquinones, flavonoids, curcumins, indigos and chlorophylls, specifically, e.g., *Impatiens balsamina*, madder, amaranth, clove, *Hispid arthraxon*, sappan, YUSONG, *Bletilla striata*, indigotin, ZAOHE, lithospermum, purple vegetables, logwood, indigo, safflower, pomegranate, *Gardenia jasminoides, Artemisia argyi, Rheum officinale, Schisandra chinensis, Radix isatidis*, bluegrass, tumeric, sophora flower bud, *Rhamnus utilis*, acorn, *Sapium sebiferum*, gallnut, chestnut oak, millet shell, lotus seed hull, persimmon, avocado, *Polygonum multiflorum*, dye yam, *Isatis indigotica, Purple perilla, Haematoxylum campechianum*, red wine, coffee, tea, Indigo naturalis, beer, lemon and *Chrysanthemum morifolium*. In the embodiments of the present invention, the mineral hair dyes include various inorganic metal salts, metal oxides and ores, specifically, e.g., cinnabar, orpiment, ochre, celestite, malachite, calaite, carbon black, golden and silver foils and corals; and the animal hair dyes include, but are not limited to, lac insects and cochineal insects.

In the embodiments of the present application, the chemical hair dyes comprise black dye 401, red dye 102, acidic complex brown RH (LUOHE RH), orange yellow, brown RH, trioxyphenylmethane azoquinoline and/or p-phenylenediamine powder.

The hair darkening dye composition comprises 1~99 parts by weight of the darkening agent, preferably 4~45 parts by weight of the darkening agent, wherein the darkening agent is selected from one or more of chitin, chitosan, gelatin, silicone oil and resin, the chitin, chitosan and gelatin all have a relative molecular mass of $2.7\times10^4$ or less, and the silicone oil and resin both have a refractive index of 1.55 or less.

In the above, the silicone oil is also referred to as an organic silicone oil, which is organic polyorganosiloxane of a chain structure with different polymerization degrees, and is preferably prepared according to the following method: adding water to dimethyl dichlorosilane for hydrolyzing to obtain a primary polycondensed ring body which is cracked and rectified to obtain a low ring, then mixing the low ring body, an end-blocking agent and a catalyst, and distilling under a reduced pressure to remove low-boiling-point substances to obtain the organic silicone oil; and the silicone oil also includes modified silicone oil or organic silicone oil derivatives. The silicone oil comprises, but is not limited to, alkyl silicone oil, hydroxyl silicone oil, amino silicone oil, phenyl silicone oil, fluorine-containing silicone oil, cyanogen-containing silicone oil, ternary block organic silicone oil and polyether modified silicone oil, specifically, e.g., methyl silicone oil, ethyl silicone oil, methyl hydrogen-containing silicone oil, methyl phenyl silicone oil, methyl chlorophenyl silicone oil, methyl ethyoxyl silicone oil, methyl trifluoropropyl silicone oil, long-chain alkyl silicone oil, cationic reactive organic silicone oil and aldehyde-free organic silicone oil; the silicone oil is preferably dimethyl silicone oil, octamethyl silicone oil, decamethyl pentasiloxane or fluorine-containing silicone oil. The resin is preferably organic fluorine resin, organic silicon resin, polyamine resin or polyurethane resin, and more preferably, is organic fluorine resin. The refractive indexes of the silicone oil and the resin are 1.55 or less. Since the refractive index of the ordinary natural fiber is about 1.62, the use of the silicone oil and resin having a refractive index of 1.55 or less as the darkening agent in the present invention may darken the color of the dyed hair. In the embodiments of the present invention, the refractive index of the silicone oil is preferably 1.40~1.45. The sources of the silicone oil and resin are not specially limited in the present invention; and in the embodiments of the present invention, the silicone oil can be amino silicone oil with the model No. SILANOL SF9188 or SILANOL SF9103.

In addition, the silicone oil or resin may also endow the dyed hair with other effects, for example, enabling the hair to have antistatic property, increasing stiffness, etc. In a preferred embodiment of the present invention, the darkening agent is silicone oil, resin and chitosan, and by using the elastic net structure of the organic silicone oil and resin, the present invention endows the chitosan film with a very high tensile strength, flexibility and water-washing resistance.

In the darkening agent of the present invention, the chitin is mainly derived from shells of the shellfish such as shrimps, crabs etc.; the chitosan, which is also called deacetylated chitin, is formed by hydrolyzing chitin under an alkaline condition to remove the acetyl group. The chitin and the chitosan are high polymers of polysaccharides, and contain a large number of hydroxyl and amino groups in the molecular structures; and the gelatin is a substance obtained by degradation of the collagen parts in the tissues of animals, such as skin, bones etc. In the present invention, by using the darkening property of the chitin, chitosan and gelatin and overcoming other defective properties under the multifunctional synergistic effect of other raw materials such as the crosslinking agent etc., the hair is enabled to have darkened color and other favorable effects during the dyeing process.

First, the present invention needs to overcome the defect that chitin, chitosan and gelatin have a low adsorption rate for such a protein fiber as hair. Hair belongs to protein fibers, and protein fibers are all amphoteric fibers containing acidic groups and alkaline groups. For the darkening agent of the present invention, such as chitosan, the molecules thereof contain a large number of —$NH_2$ and —OH groups, which have a good affinity with hair fibers and can be dissolved into the interior of hair fibers, and the hair fibers bond to the active groups, —OH and —$NH_2$, by means of hydrogen bonds or covalent bonds. However, the chitosan molecules bond to the ionized carboxyl group on the hair fibers in an acidic bath, making the hair fibers positively charged, and this will hinder continued adsorption and large-scale adsorption of chitosan. Due to adsorption quantity is too small, the thickness of the film formed is affected, hardly achieving the expected effects such as darkening. The applicant has discovered, by researches, that for such darkening agent as chitin or chitosan, the smaller relative molecular weight is more advantageous to the facilitation of the diffusion thereof in the hair fibers, so that the adsorption rate thereof is increased, thereby darkening the hair better. Thus, chitin or chitosan must be degraded into an oligosaccharide having a certain molecular weight in order to have good adsorbability and durability. In the present invention, the chitin, chitosan and gelatin all have a relative molecular mass of $2.7\times10^4$ or less, preferably $2.0\times10^4$~$2.6\times10^4$; and in the present invention, the commercial products of chitin, chitosan and gelatin can just be used.

In a preferred embodiment of the present invention, the darkening agent is selected from chitin, chitosan or gelatin; and the darkening agent is preferably prepared by degradation using a degradation agent. In the present invention, the degradation agent is preferably selected from an acidic degradation agent, an oxidative degradation agent or an enzyme degradation agent; specifically, the degradation agent includes, but is not limited to, phosphoric acid ($H_3PO_4$), hydrochloric acid (HCl), hydrofluoric acid (HF), nitric acid ($HNO_3$), acetic acid ($CH_3COOH$), hydrogen peroxide ($H_2O_2$), ozone, sodium perborate, chitosanase, chitin deacetylase (chitinase), lysozyme, esterase, lipase, hemicellulase, cellulase, carbohydrase, protease or pectinase.

In one embodiment of the present invention, the darkening agent is prepared by an acid degradation method, viz. degrading chitosan etc. with an acid, which is the most basic and simple method. Specifically, chitosan can be severely degraded under the effect of an inorganic strong acid such as HCl, $H_3PO_4$, HF and $HNO_3$, utilizing that a plurality of free amino groups present in the chitosan molecules bind to $H^+$ in the solution, to cause the breakage of the intermolecular and intramolecular hydrogen bonds in the chitosan molecules, so that the molecular structures are stretched, and the long-chain parts are susceptible to experience the breakage of glycosidic bonds, forming a plurality of molecular fragments having different polymerization degrees.

In another embodiment of the present invention, the darkening agent is prepared by an oxidative degradation method. For example, $H_2O_2$, which is an oxidizer with strong oxidizing ability, has the advantages of no toxicity and no by-products when used to oxidize and degrade chitosan, and can always obtain the low-molecular-weight chitosan under acidic, alkaline and neutral conditions. The degradation by $H_2O_2$ is achieved by using various free radicals $HO_2$., HO. and (O) formed by ionization of $H_2O_2$ in an aqueous solution, in which the highly active HO. and the nascent (O), which have an extremely strong oxidation property, attack the β(1, 4) glycosidic bonds with active $NH^{2+}$ on chitosan to depolymerize the same.

In another embodiment of the present invention, the darkening agent is prepared by an enzymolysis (enzyme degradation) method. Compared with other degradation methods, the enzyme degradation method has the advantages, such as no side reactions, mild degradation conditions, easy control of the degradation process and the distribution of relative molecular weight of the degradation products, high bioactivity of the prepared oligochitosan and no necessity to desalt the products. According to different enzymes used, there are specific enzyme degradation (such as chitosanase and lysozyme) and non-specific enzyme degradation (such as lipase, protease and cellulase). In addition, an ozone method, a sodium perborate method, a periodate method, a hypohalite method and physical methods such as microwave, ray radiation, etc. may also be used to degrade chitin or chitosan, so as to prepare the darkening agent of the present invention.

Second, the present invention needs to overcome the defects of poor adsorption fastness and wash durability: the darkening agents such as chitosan cannot endure drying, are poor in wet washing fastness, thus upon rinsed, they are very susceptible to loss, and cannot achieve the expected effects such as darkening. In order to improve the durability of the darkening effect of chitosan, particularly the washing fastness of the wet film, a crosslinking agent is used in the present invention, and by means of electrostatic attraction and complexation with hair fibers, hydroxyl groups are introduced into the chitosan film, thereby improving the adsorption fastness of chitosan. Furthermore, bonding of a complex with good hygroscopicity onto the chitosan film may improve hygroscopicity and moisture penetrability of the chitosan film, thereby improving the moisture resistance and wet washing fastness of the chitosan film, which enables certain durability of the effects such as darkening.

The hair darkening dye composition provided by the present invention comprises 2~98 parts by weight of the crosslinking agent, preferably 5~40 parts by weight of the crosslinking agent. In the present invention, the crosslinking agent is preferably selected from one or more of cyanaldehyde, magnesium chloride, citric acid, glyoxal, crosslinking agent EH, polyethylene glycol and antistatic agent A-2ST. In one embodiment of the present invention, glyoxal is used as the crosslinking agent, and the stable mixture emulsion thereof has strong adsorption ability for hair, and can endow the chitosan film with good air permeability, moisture permeability, hygroscopicity and bending rigidity.

The hair darkening dye composition comprises 2~98 parts by weight of an emulsifier, preferably 10~80 parts by weight of an emulsifier. The emulsifier mainly includes a cationic emulsifier, an anionic emulsifier, a zwitterionic emulsifier and a nonionic emulsifier. The present invention preferably uses a zwitterionic emulsifier and/or a nonionic emulsifier as the emulsifier. In one embodiment of the present invention, the emulsifier is an organosilicon emulsifier, such as an amino silicone oil emulsifier and a dimethyl silicone oil emulsifier.

The hair darkening dye composition comprises 2~98 parts by weight of a dyeing auxiliary, preferably 10~80 parts by weight of a dyeing auxiliary. In the present invention, the dyeing auxiliary is preferably selected from edible salt, sodium sulphate, alum, melanterite, chalcanthite, acetic acid, sodium carbonate or sodium bicarbonate.

The hair darkening dye composition comprises 0.1~40 parts by weight of a pH regulator, preferably 1~30 parts by weight of a pH regulator. In a preferred embodiment of the present invention, the pH regulator is selected from an organic acid, an inorganic weak acid, an organic base or an inorganic weak base. The pH regulator can also be divided into acidic regulator and alkaline regulator, wherein the examples of the acidic regulator include citric acid, sorbic acid, lactic acid, tartaric acid, malic acid, metatartaric acid, phosphoric acid, acetic acid (ethanoic acid), hydrochloric acid, oxalic acid and fumaric acid; and the examples of the alkaline regulator include sodium bicarbonate, disodium hydrogen phosphate, sodium carbonate, sodium citrate, potassium citrate, trisodium hydrogen carbonate (sodium sesquicarbonate) and monosodium citrate.

In order to impart more functions, the hair darkening dye composition preferably further comprises 2~98 parts by weight of an additive. The additive can be selected from one or more of a leveling agent, a penetrant, an antistatic agent, an anti-corrosion antibacterial agent and an essence, or can be other functional additives.

Specifically, the leveling agent includes, but is not limited to, peregal O, the leveling agent OP and the leveling agent 102. The antistatic agent includes a friction coefficient reducing antistatic agent, an electrically conductive antistatic agent, an ionic antistatic agent and a nonionic antistatic agent, and the ionic antistatic agent includes an anionic antistatic agent, a cationic antistatic agent and a zwitterionic antistatic agent, for example, polyethylene glycol, sorbitol, polyoxyethylenated castor oil, polyoxyethylene laurate, polyethylene glycol, sulfonate, acidic phosphate, neutral phosphate, amine salts, quaternary ammonium salts, alkyl imidazoline, polyols, polyol esters and ethylene oxide adduct of alkylamine. The anti-corrosion antibacterial agent can be one or more of rare earth and derivatives thereof, nisin, natamycin, red yeast rice extract (HONGQUMISU), lysozyme, protamine, propolis, agaro-oligosaccarides, eucommin, benzoic acid, sodium benzoate, potassium sorbate, sodium dehydroacetate and sodium diacetate.

The hair darkening dye composition provided by the present invention can be prepared according to the following method:

weighing the following raw materials:

2~98 parts by weight of a hair dye;

1~99 parts by weight of a darkening agent, which is selected from one or more of chitin, chitosan, gelatin, silicone oil and resin, wherein the chitin, chitosan and gelatin all have a relative molecular mass of $2.7\times10^4$ or less, and the silicone oil and resin both have a refractive index of 1.55 or less, 2~98 parts by weight of a crosslinking agent, 2~98 parts by weight of an emulsifier, 2~98 parts by weight of a dyeing auxiliary, and 0.1~40 parts by weight of a pH regulator; and mixing the raw materials at a temperature of 0~200° C., to obtain the hair darkening dye composition.

In a preferred embodiment of the present invention, the mixing specifically comprises:

emulsifying the darkening agent into an emulsion by using the emulsifier;

mixing the hair dye, the crosslinking agent and the dyeing auxiliary to obtain a mixture solution;

regulating the pH value of the mixture solution to 1~10 by using the pH regulator; and mixing the emulsion with the mixture solution whose pH value has been regulated, to obtain the hair darkening dye composition.

In the present invention, the mixing, emulsifying etc. are technical means well known to a person skilled in the art; and the temperature for the mixing is preferably 20° C.~100° C.

When in use, the hair dyeing methods of the hair dye composition containing a pure natural hair dye include: one-pack dyeing method: 1) the use amount of the hair dye composition: 20~30 grams for short hair, and 50~60 grams for medium-length hair or long hair; and 2) operation method: applying the hair dye composition to hair, optionally wrapping the hair with a hot towel for 30~40 minutes, and then rinsing off with warm water.

Two-pack dyeing method: 1) the use amount of the hair dye composition: 20~30 grams for short hair, and 50~60 grams for medium-length hair or long hair; and 2) operation method: mixing the hair dye composition and the dyeing auxiliary at a ratio of 1:1, stirring to mix evenly, applying to hair evenly, optionally wrapping the hair with a hot towel for 3040 minutes, and then rinsing off with warm water.

The hair dyeing method of a hair dye composition containing a chemical hair dye includes: 1) the use amount of the hair dye composition: 10~20 grams for short hair, and 20~30 grams for medium-length hair or long hair; and 2) dyeing method: applying the hair dye composition to hair, keeping for 10~30 minutes, and then rinsing off with warm water.

The hair darkening dye composition obtained by the present invention is mainly composed of 2~98 parts by weight of a hair dye, 1~99 parts by weight of a darkening agent, 2~98 parts by weight of a crosslinking agent, 2~98 parts by weight of an emulsifier, 2~98 parts by weight of a dyeing auxiliary and 0. 1~40 parts by weight of a pH regulator. In the present invention, the hair dye can dye hair into a color with a certain depth; under the effects of the darkening agent, the crosslinking agent etc., the unsaturated color dyed by the pure natural hair dye can be deepened, and a saturated color with a sufficient depth is finally obtained, or the use amount of a chemical hair dye can be greatly reduced; moreover, the hair dyeing time can be shortened and the hair dyeing temperature can be reduced, thereby relatively reducing the harm to the human body, furthermore, the dyeing fastness can be improved, prolonging the dyeing interval and reducing the number of the times of repeated hair dyeing. Thus, under the synergistic and comprehensive effects of all the raw materials, the hair darkening dye composition provided by the present invention has the properties of color darkening and fixation, such that an unsaturated color dyed by a pure natural hair dye is deepened into a saturated color and a saturated color may be achieved by a relatively small amount of a chemical hair dye.

In addition, the hair darkening dye composition of the present invention further has other functions as follows: the present invention has overcome the defects such as stiffness of the darkening agent, and enables the hair darkening dye composition to have the function of hair comforting agent, having the effects of making the dyed hair moisturized, silky, fluffy etc. The present invention can improve the hair dyeing fastness of the hair darkening dye composition by using the excellent color fixation effect of the darkening agent. The present invention can make it difficult for the dyed hair to generate static electricity, endow the dyed hair with better loose and smooth properties, and also enable the dyed hair to have bacteriostatic, antibacterial and immune effects.

In order to further illustrate the present invention, the hair darkening dye composition provided by the present invention will be described in detail in conjunction with the examples below. However, these examples shall not be construed as a limitation on the protection scope of the present invention.

Example 1

20 parts by weight of chitin (with a relative molecular mass of $3\times10^5$~$7\times10^5$) are degraded to have a relative molecular mass of $2.7\times10^4$ by using 10 parts by weight of chitinase, obtaining a darkening agent.

20 parts by weight of the darkening agent are emulsified into an emulsion by using 40 parts by weight of an emulsifier (model No. AEO9, purchased from PetroChina Jilin Petrochemical Company).

50 parts by weight of indigotin, 5 parts by weight of the crosslinking agent EH and 1 part by weight of alum are weighed and mixed at 20° C. to obtain a mixture solution.

The pH value of the mixture solution is regulated to 4~5 by using 1 part by weight of acetic acid.

The emulsion and the mixture solution whose pH value has been regulated are mixed at 20° C., obtaining a hair darkening dye composition.

Comparative Example 1

20 parts by weight of chitin (with a relative molecular mass of $3\times10^5$~$7\times10^5$) are emulsified into an emulsion by using 30 parts by weight of an emulsifier (model No. AEO3, purchased from PetroChina Jilin Petrochemical Company).

50 parts by weight of indigotin and 1 part by weight of alum are weighed and mixed at 20° C. to obtain a mixture solution.

The pH value of the mixture solution is regulated to 5~6 by using 1 part by weight of acetic acid.

The emulsion and the mixture solution whose pH value has been regulated are mixed at 20° C., obtaining a hair dye composition.

Example 2

The organosilicon resin (purchased from Shandong Dayi Chemical Co. Ltd.) having a refractive index of 1.3868 is used as the darkening agent.

30 parts by weight of the darkening agent are emulsified into an emulsion by using 35 parts by weight of an amino silicone oil emulsifier (an environment-friendly emulsifier with the model No. EXG-101, purchased from Shanghai Honesty Fine Chemical Co., Ltd.).

2 parts by weight of the red dye 102, 10 parts by weight of a crosslinking agent and 20 parts by weight of a dyeing auxiliary are weighed and mixed at 20° C. to obtain a mixture solution.

The pH value of the mixture solution is regulated to 3~4 by using 1 part by weight of acetic acid.

The emulsion and the mixture solution whose pH value has been regulated are mixed at 20° C., obtaining a hair darkening dye composition.

Comparative Example 2

2 parts by weight of the red dye 102 and 10 parts by weight of a dyeing auxiliary are weighed and mixed at 20° C. to obtain a mixture solution.

The pH value of the mixture solution is regulated to 7~8 by using 1 part by weight of acetic acid.

50 parts by weight of an amino silicone oil emulsifier (amino silicone oil emulsifier AMM or AMH, purchased from Jiangsu Haian Petroleum Chemical Factory) and the mixture solution whose pH value has been regulated are mixed at 20° C., obtaining a hair dye composition.

Example 3

Organic fluororesin (purchased from Dalian Botai Co., Ltd.) having a refractive index of 1.38 is used as a darkening agent.

30 parts by weight of the darkening agent are emulsified into an emulsion by using 55 parts by weight of an emulsifier (dimethyl silicone oil emulsifier 1# or 2#, purchased from Jiangsu Haian Petroleum Chemical Factory).

2 parts by weight of orange yellow, 10 parts by weight of citric acid and 40 parts by weight of dyeing auxiliary are weighed and mixed at 20° C. to obtain a mixture solution.

The pH value of the mixture solution is regulated to 6~7 by using 1 part by weight of acetic acid.

The emulsion and the mixture solution whose pH value has been regulated are mixed at 20° C., obtaining a hair darkening dye composition.

Comparative Example 3

2 parts by weight of orange yellow and 20 parts by weight of dyeing auxiliary are weighed and mixed at 20° C. to obtain a mixture solution.

The pH value of the mixture solution is regulated to 2~3 by using 1 part by weight of acetic acid.

36 parts by weight of an emulsifier (a carnauba wax emulsifier, purchased from Jiangsu Haian Petroleum Chemical Factory) and the mixture solution whose pH value has been regulated are mixed at 20° C., obtaining a hair dye composition.

Example 4

Gelatin (industrial gelatin, purchased from Shanghai Lubo Gelatin Co., Ltd.) is used as a darkening agent.

10 parts by weight of the darkening agent are emulsified into an emulsion by using 42 parts by weight of an emulsifier (reactive emulsifier NRS-1030, purchased from Shanghai Honesty Fine Chemical Co., Ltd.).

30 parts by weight of malachite, 5 parts by weight of polyethylene glycol and 1 part by weight of melanterite are weighed and mixed at 20° C. to obtain a mixture solution.

The pH value of the mixture solution is regulated to 4~5 by using 1 part by weight of hydrochloric acid.

The emulsion and the mixture solution whose pH value has been regulated are mixed at 20° C., obtaining a hair darkening dye composition.

Comparative Example 4

30 parts by weight of malachite and 1 part by weight of melanterite are weighed and mixed at 20° C. to obtain a mixture solution.

The pH value of the mixture solution is regulated to 6~7 by using 1 part by weight of hydrochloric acid.

40 parts by weight of an emulsifier (narrow-distribution environment-friendly emulsifier GS-730 or GS-930, purchased from Shanghai Honesty Fine Chemical Co., Ltd.) and the mixture solution whose pH value has been regulated are mixed at 20° C., obtaining a hair dye composition.

Example 5

Dimethyl silicone oil (purchased from Shandong Dayi Chemical Co. Ltd.) having a refractive index of 1.43 is used as a darkening agent.

30 parts by weight of the darkening agent are emulsified into an emulsion by using 10 parts by weight of a nonionic emulsifier (model No. TX-40, purchased from Jiangsu Haian Petroleum Chemical Factory).

50 parts by weight of *Rhamnus utilis,* 15 parts by weight of a crosslinking agent and 1 part by weight of alum are weighed and mixed at 20° C. to obtain a mixture solution.

The pH value of the mixture solution is regulated to 6~7 by using 1 part by weight of sodium citrate.

The emulsion and the mixture solution whose pH value has been regulated are mixed at 20° C., obtaining a hair darkening dye composition.

Comparative Example 5

50 parts by weight of *Rhamnus utilis* and 1 part by weight of alum are weighed and mixed at 20° C. to obtain a mixture solution.

The pH value of the mixture solution is regulated to 5~6 by using 1 part by weight of sodium citrate.

10 parts by weight of a nonionic emulsifier (model No. NP-4, purchased from Jiangsu Haian Petroleum Chemical Factory) and the mixture solution whose pH value has been regulated are mixed at 20° C., obtaining a hair dye composition.

Example 6

Amino silicone oil (purchased from Shandong Dayi Chemical Co. Ltd.) having a refractive index of 1.35 is used as a darkening agent.

30 parts by weight of the darkening agent are emulsified into an emulsion by using 5 parts by weight of an anionic emulsifier (an environment-friendly anionic reactive emulsifier, purchased from Nanjing Xinhai Trading Co., Ltd.).

40 parts by weight of lithospermum, 5 parts by weight of glyoxal and 1 part by weight of chalcanthite are weighed and mixed at 20° C. to obtain a mixture solution.

The pH value of the mixture solution is regulated to 4~5 by using 1 part by weight of tartaric acid.

The emulsion and the mixture solution whose pH value has been regulated are mixed at 20° C., obtaining a hair darkening dye composition.

Comparative Example 6

40 parts by weight of lithospermum and 1 part by weight of chalcanthite are weighed and mixed at 20° C. to obtain a mixture solution.

The pH value of the mixture solution is regulated to 8~9 by using 1 part by weight of tartaric acid.

5 parts by weight of an anionic emulsifier (model No. DOWFAX 2A1, purchased from Guangzhou Fengbaishun Trading Co., Ltd.) and the mixture solution whose pH value has been regulated are mixed at 20° C., obtaining a hair dye composition.

Example 7

The hair darkening dye compositions obtained in Examples 1~6 and the hair dye compositions obtained in Comparative Examples 1~6 are used to dye hair according to the methods described above. The comparison of the colors of the dyed hair is shown in Table 1. Table 1 shows a comparison of the hair dyeing results of the hair dye compositions provided by Examples 1~6 of the present invention and the hair dye compositions provided by Comparative Examples 1~6.

TABLE 1

Comparison of hair dyeing results of the hair dye compositions provided by Examples 1~6 of the present invention and the hair dye compositions provided by Comparative Examples 1~6

| | Example 1 | Comparative Example 1 | Example 2 | Comparative Example 2 | Example 3 | Comparative Example 3 |
|---|---|---|---|---|---|---|
| Color of the dyed hair | dark blue | sky blue | red | pink | nacarat | saffron |
| | Example 4 | Comparative Example 4 | Example 5 | Comparative Example 5 | Example 6 | Comparative Example 6 |
| Color of the dyed hair | peacock blue | aqua blue | dark green | jade green | purple | bisque |

Also, testing of hair comfort has been conducted for the hair dye compositions obtained in Example 1 and Comparative Example 1. The testing methods and results are shown in Table 2. Table 2 shows the effects of the hair dye compositions provided by Example 1 of the present invention and Comparative Example 1 on hair comfort.

TABLE 2

Effects of the hair dye compositions provided by Example 1 of the present invention and Comparative Example 1 on hair comfort

| | Water resistance/ Pa | Water repellency (%) | Moisture permeability/ $g \cdot m^{-2} \cdot d^{-1}$ | Hydroscopicity and diffusivity | Antibacterial and deodorant properties | Crumpling resistance (times) |
|---|---|---|---|---|---|---|
| Hair dye composition of Example 1 | 19600 | 100 | 8000~ 10000 | excellent | | Dry: 2000 Wet: 500 |
| Traditional dye of Comparative Example 1 | 9800 | 90 | 4000 or more | none | none | Dry: 1850 Wet: 480 |
| Testing | JIS-L109 | JIS-L1092 | JIS-L1092 | | Bacteria | JISK- |

TABLE 2-continued

Effects of the hair dye compositions provided by Example 1 of the present invention and Comparative Example 1 on hair comfort

| | Water resistance/ Pa | Water repellency (%) | Moisture permeability/ g · m$^{-2}$ · d$^{-1}$ | Hydro-scopicity and diffusivity | Anti-bacterial and deodorant properties | Crumpling resistance (times) |
|---|---|---|---|---|---|---|
| methods | (Hydro-static pressure method) | (Spraying method) | (CUP method) | | number determi-nation method | 6772SC OTT method |

As can be seen from the above examples and comparative examples, the hair darkening dye composition provided by the present invention is mainly composed of the following raw materials: 2~98 parts by weight of a hair dye, 1~99 parts by weight of a darkening agent, 2~98 parts by weight of a crosslinking agent, 2~98 parts by weight of an emulsifier, 2~98 parts by weight of a dyeing auxiliary, and 0.1~40 parts by weight of a pH regulator, wherein the darkening agent is selected from one or more of chitin, chitosan, gelatin, silicone oil and resin, the chitin, chitosan and gelatin all have a relative molecular mass of $2.7\times10^4$ or less, and the silicone oil and resin both have a refractive index of 1.55 or less. Under the synergistic and comprehensive effects of all the raw materials, the hair darkening dye composition provided by the present invention has a darkening property and can achieve a saturated color with a relatively small amount.

In addition, the present invention has overcome the defects such as stiffness of the darkening agent, and enables the hair darkening dye composition to have the function of hair comforting agent, and have the effects of making the dyed hair moisturized, silky, fluffy etc. The present invention can improve the hair dyeing fastness of the hair darkening dye composition by using the excellent color fixation effect of the darkening agent. The present invention can make it difficult for the dyed hair to generate static electricity, endow the dyed hair with better loose and smooth properties, and also enable the dyed hair to have bacteriostatic, antibacterial and immune effects.

The above descriptions are merely preferred embodiments of the present invention, and it should be noted that, for a person skilled in the art, several improvements and modifications may also be made without departing from the principles of the present invention, and these improvements and modifications should be covered in the protection scope of the present invention.

What is claimed is:

1. A hair darkening dye composition, comprising:

2~98 parts by weight of a hair dye;

1~99 parts by weight of a darkening agent, which is one or more selected from the group consisting of chitin, chitosan, gelatin, silicone oil and resin, wherein the chitin, chitosan and gelatin all have a relative molecular mass of $2.7\times10^4$ or less, and the silicone oil and resin both have a refractive index of 1.55 or less;

2~98 parts by weight of a crosslinking agent;

2~98 parts by weight of an emulsifier;

2~98 parts by weight of a dyeing auxiliary; and 0.1~40 parts by weight of a pH regulator.

2. The hair darkening dye composition according to claim 1, wherein the crosslinking agent is one or more selected from the group consisting of cyanaldehyde, magnesium chloride, citric acid, glyoxal, and polyethylene glycol.

3. The hair darkening dye composition according to claim 1, wherein the hair darkening dye composition comprises 5~40 parts by weight of the crosslinking agent.

4. The hair darkening dye composition according to claim 1, wherein the hair darkening dye composition comprises 4~45 parts by weight of the darkening agent.

5. The hair darkening dye composition according to claim 1, wherein the darkening agent is selected from the group consisting of chitin, chitosan and gelatin; and the darkening agent is prepared by degradation using a degradation agent, wherein the degradation agent is selected from the group consisting of an acid degradation agent, an oxidative degradation agent and an enzyme degradation agent.

6. The hair darkening dye composition according to claim 1, wherein the pH regulator is selected from the group consisting of an organic acid, an inorganic weak acid, an organic base and an inorganic weak base.

7. The hair darkening dye composition according to claim 1, wherein the hair darkening dye composition comprises 2~60 parts by weight of the hair dye; and the hair dye is selected from the group consisting of pure natural hair dyes and chemical hair dyes.

8. The hair darkening dye composition according to claim 1, wherein the emulsifier is selected from the group consisting of a zwitterionic emulsifier and a nonionic emulsifier.

9. The hair darkening dye composition according to claim 1, wherein the dyeing auxiliary is selected from the group consisting of edible salt, sodium sulphate, alum, melanterite, chalcanthite, acetic acid, sodium carbonate and sodium bicarbonate.

10. The hair darkening dye composition according to claim 1, wherein the hair darkening dye composition further comprises 2~98 parts by weight of an additive; and the additive is one or more selected from the group consisting of a leveling agent, an antistatic agent, an anti-corrosion antibacterial agent and an essence.

11. The hair darkening dye composition according to claim 2, wherein the hair darkening dye composition further comprises 2~98 parts by weight of an additive; and the additive is one or more selected from the group consisting of a leveling agent, an antistatic agent, an anti-corrosion antibacterial agent and an essence.

12. The hair darkening dye composition according to claim 3, wherein the hair darkening dye composition further comprises 2~98 parts by weight of an additive; and the additive is one or more selected from the group consisting of a leveling agent, an antistatic agent, an anti-corrosion antibacterial agent and an essence.

13. The hair darkening dye composition according to claim 4, wherein the hair darkening dye composition further comprises 2~98 parts by weight of an additive; and the additive is one or more selected from the group consisting of a leveling agent, an antistatic agent, an anti-corrosion antibacterial agent and an essence.

14. The hair darkening dye composition according to claim 5, wherein the hair darkening dye composition further comprises 2~98 parts by weight of an additive; and the additive is one or more selected from the group consisting of a leveling agent, an antistatic agent, an anti-corrosion antibacterial agent and an essence.

15. The hair darkening dye composition according to claim 6, wherein the hair darkening dye composition further comprises 2~98 parts by weight of an additive; and the additive is one or more selected from the group consisting of a leveling agent, an antistatic agent, an anti-corrosion antibacterial agent and an essence.

16. The hair darkening dye composition according to claim 7, wherein the hair darkening dye composition further comprises 2~98 parts by weight of an additive; and the additive is one or more selected from the group consisting of a leveling agent, an antistatic agent, an anti-corrosion antibacterial agent and an essence.

17. The hair darkening dye composition according to claim 8, wherein the hair darkening dye composition further comprises 2~98 parts by weight of an additive; and the additive is one or more selected from the group consisting of a leveling agent, an antistatic agent, an anti-corrosion antibacterial agent and an essence.

18. The hair darkening dye composition according to claim 9, wherein the hair darkening dye composition further comprises 2~98 parts by weight of an additive; and the additive is one or more selected from the group consisting of a leveling agent, an antistatic agent, an anti-corrosion antibacterial agent and an essence.

* * * * *